US011191696B2

(12) United States Patent
Aragon

(10) Patent No.: US 11,191,696 B2
(45) Date of Patent: Dec. 7, 2021

(54) VAPORIZING AND VAPOR HEATING ASSEMBLY AND PERSONAL CARE APPLIANCES INCLUDING THE SAME

(71) Applicant: L'Oreal, Paris (FR)

(72) Inventor: Joel Timothy Aragon, Snohomish, WA (US)

(73) Assignee: L'Oreal, Paris (FR)

( * ) Notice: Subject to any disclaimer, the term of this patent is extended or adjusted under 35 U.S.C. 154(b) by 318 days.

(21) Appl. No.: 15/476,352

(22) Filed: Mar. 31, 2017

(65) Prior Publication Data

US 2018/0280233 A1  Oct. 4, 2018

(51) Int. Cl.

| | |
|---|---|
| *A61H 33/06* | (2006.01) |
| *A46B 13/04* | (2006.01) |
| *A46B 11/08* | (2006.01) |
| *B05B 17/06* | (2006.01) |
| *B05B 7/16* | (2006.01) |
| *A61M 35/00* | (2006.01) |
| *A61F 7/00* | (2006.01) |
| *A61B 17/32* | (2006.01) |

(Continued)

(52) U.S. Cl.
CPC .............. *A61H 33/06* (2013.01); *A46B 7/04* (2013.01); *A46B 11/0062* (2013.01); *A46B 11/0065* (2013.01); *A46B 11/08* (2013.01); *A46B 13/008* (2013.01); *A46B 13/04* (2013.01); *A46B 15/003* (2013.01); *A61B 17/32* (2013.01); *A61F 7/0085* (2013.01); *A61M 35/003* (2013.01); *B05B 7/1686* (2013.01); *B05B 17/0607* (2013.01); *A46B 2200/1006* (2013.01); *A61B 2017/320004* (2013.01); *A61F 2007/0062* (2013.01); *A61H 2033/068* (2013.01); *H04L 63/0421* (2013.01); *H04L 63/0428* (2013.01)

(58) Field of Classification Search
CPC .... A61H 33/06; A61H 33/063; A61H 33/065; A61H 33/12; A61H 2201/0153; A61H 2201/0228; A61H 2201/5038; A46B 15/003; A46B 11/08; A46B 13/008; A46B 13/04; A46B 11/0062; A46B 11/0065; B05B 17/0607; B05B 7/1686; B05B 7/1693
See application file for complete search history.

(56) References Cited

U.S. PATENT DOCUMENTS 1,756,033 A  *  4/1930  Nordan ................. F24H 3/0417
392/361
2,648,567 A  *  8/1953  Brennan .................... B05B 7/18
239/81

(Continued)

OTHER PUBLICATIONS

"Adjacent." Merriam-Webster.com. 2020. https://www.merriam-webster.com (Sep. 15, 2020). (Year: 2020).*

(Continued)

*Primary Examiner* — Alex M Valvis
*Assistant Examiner* — Christopher R Dandridge
(74) *Attorney, Agent, or Firm* — Christensen O'Connor Johnson Kindness PLLC

(57) ABSTRACT

A vaporizing and vapor heating assembly includes at least one vaporizing element fluidically coupled to at least one reservoir and configured to discharge vapor and a heater assembly operably coupled to the at least one vaporizing element. The heater assembly including at least one heating element configured to heat the discharged vapor.

19 Claims, 5 Drawing Sheets

(51) Int. Cl.
  *A46B 13/00* (2006.01)
  *A46B 15/00* (2006.01)
  *A46B 11/00* (2006.01)
  *A46B 7/04* (2006.01)
  *H04L 29/06* (2006.01)

(56) References Cited

U.S. PATENT DOCUMENTS

| | | | |
|---|---|---|---|
| 5,046,942 A * | 9/1991 | Gellert | B29C 45/2737 |
| | | | 219/523 |
| 5,688,421 A * | 11/1997 | Walton | B05C 17/00526 |
| | | | 219/230 |
| 6,220,579 B1 | 4/2001 | Chen | |
| 7,157,816 B2 | 1/2007 | Pilcher et al. | |
| 7,386,906 B2 | 6/2008 | Roth et al. | |
| 7,786,626 B2 | 8/2010 | Reishus et al. | |
| 8,157,753 B2 * | 4/2012 | Nichols | A61H 33/12 |
| | | | 601/17 |
| 8,756,549 B2 | 6/2014 | Graf et al. | |
| 8,758,309 B2 | 6/2014 | Nakamura | |
| 9,462,873 B2 | 10/2016 | Casasanta, III | |
| 9,814,295 B2 * | 11/2017 | Chiasson | A61M 35/003 |
| 2004/0231668 A1 | 11/2004 | Kates | |
| 2008/0223953 A1 * | 9/2008 | Tomono | A01M 1/205 |
| | | | 239/102.2 |
| 2008/0290189 A1 | 11/2008 | Levi | |
| 2009/0247913 A1 | 10/2009 | Nichols | |
| 2012/0233798 A1 | 9/2012 | Brewer et al. | |
| 2016/0331106 A1 * | 11/2016 | Khormaei | A46B 11/08 |

OTHER PUBLICATIONS

International Search Report dated Jun. 18, 2018, issued in corresponding International Application No. PCT/US2018/016228, filed Jan. 31, 2018, 19 pages.

International Preliminary Report on Patentability and Written Opinion dated Oct. 10, 2019, issued in corresponding International Application No. PCT/US2018/016228, filed Jan. 31, 2018, 13 pages.

First Office Action dated Sep. 17, 2020, issued in corresponding Chinese Application No. 201880023039.1, filed Jan. 31, 2018, 10 pages.

* cited by examiner

US 11,191,696 B2

VAPORIZING AND VAPOR HEATING ASSEMBLY AND PERSONAL CARE APPLIANCES INCLUDING THE SAME

SUMMARY

In an embodiment, a vaporizing and vapor heating assembly includes at least one vaporizing element configured to discharge vapor from at least one reservoir containing a fluid and a heater assembly configured to heat the discharged vapor.

In an embodiment, a vaporizing and vapor heating assembly includes at least one vaporizing element fluidically coupled to at least one reservoir and configured to discharge vapor and a heater assembly operably coupled to the at least one vaporizing element. The heater assembly including at least one heating element configured to heat the discharged vapor.

In an embodiment, the at least one vaporizing element is a piezoelectric element.

In an embodiment, the piezoelectric element is in fluid communication with the at least one reservoir containing the fluid.

In an embodiment, the heater assembly includes at least one tapered heating element positioned near the at least one vaporizing element such that the vapor passes through the at least one tapered heating element when discharged.

In an embodiment, the assembly further includes a replaceable cartridge including one or more fluid reservoirs fluidically coupled to the at least one vaporizing element.

In an embodiment, the assembly further includes discharge vapor circuitry operably coupled to the at least one vaporizing element and configured to generate a discharge vapor responsive to one or more inputs indicative of a cartridge identification.

In an embodiment, the assembly further includes discharge vapor circuitry operably coupled to the at least one vaporizing element and configured to generate a discharge vapor and vapor heating circuitry operably coupled to the heater subassembly and configured to heat the discharged vapor.

In an embodiment, the discharge vapor circuitry comprises one or more piezo ultrasonic atomizers configured to discharge vapor from the at least one reservoir responsive to at least one input indicative of a discharge rate.

In an embodiment, the vapor heating circuitry activates the heater subassembly responsive to at least one input indicative of activation of the at least one vaporizing element.

In an embodiment, the vapor heating circuitry includes at least one heating element configured to be heated between at least first and second temperatures.

In an embodiment, the discharge vapor circuitry includes circuitry configured to activate the at least one vaporizing element when the at least one heating element reaches the first temperature.

In an embodiment, the discharge vapor circuitry includes circuitry configured to deactivate the heater subassembly when the at least one heating element reaches the second temperature.

In an embodiment, a personal care appliance includes an appliance body having a personal care portion, at least one vaporizing element fluidically coupled to at least one reservoir and configured to discharge vapor, and a heater assembly operably coupled to the at least one vaporizing element. The heater assembly includes at least one heating element configured to heat the discharged vapor.

In an embodiment, the appliance further includes circuitry configured to exchange encrypted and anonymized personal care appliance information with a remote network.

In an embodiment, the appliance further includes circuitry configured to detect a client device associated with the personal care appliance and to exchange encrypted and anonymized information with the client device.

In an embodiment, the appliance further includes circuitry configured to detect a client device associated with the personal care appliance and to exchange vaporizing element control information with the client device.

In an embodiment, the at least one vaporizing element is a piezoelectric element.

In an embodiment, the piezoelectric element is in fluid communication with the at least one reservoir containing the fluid.

In an embodiment, the heater assembly includes at least one tapered heating element positioned near the at least one vaporizing element such that the vapor passes through the at least one tapered heating element when discharged.

In an embodiment, the appliance further includes a replaceable cartridge including one or more fluid reservoirs fluidically coupled to the at least one vaporizing element.

In an embodiment, the appliance further includes discharge vapor circuitry operably coupled to the at least one vaporizing element and configured to generate a discharge vapor responsive to one or more inputs indicative of a cartridge identification.

In an embodiment, the appliance further includes discharge vapor circuitry operably coupled to the at least one vaporizing element and configured to generate a discharge vapor and vapor heating circuitry operably coupled to the heater subassembly and configured to heat the discharged vapor.

In an embodiment, the discharge vapor circuitry comprises one or more piezo ultrasonic atomizers configured to discharge vapor from the at least one reservoir responsive to at least one input indicative of a discharge rate.

In an embodiment, the vapor heating circuitry activates the heater subassembly responsive to at least one input indicative of activation of the at least one vaporizing element.

In an embodiment, the vapor heating circuitry includes at least one heating element configured to be heated between at least first and second temperatures.

In an embodiment, the discharge vapor circuitry includes circuitry configured to activate the at least one vaporizing element when the at least one heating element reaches the first temperature.

In an embodiment, the discharge vapor circuitry includes circuitry configured to deactivate the heater subassembly when the at least one heating element reaches the second temperature.

In an embodiment, the appliance further includes drive assembly circuitry configured to activate the personal care portion.

In an embodiment, the discharge vapor circuitry activates the at least one vaporizing element upon activation of the personal care portion.

In an embodiment, the personal care portion is a brush head assembly having bristles extending from a base.

In an embodiment, the brush head assembly includes at least one open area defined within the bristles that is aligned with the at least one vaporizing element.

In an embodiment, the base of the brush head assembly is removably attachable to the appliance body.

In an embodiment, the at least one vaporizing element is a piezoelectric element.

In an embodiment, the piezoelectric element is in fluid communication with the at least one reservoir containing the fluid.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
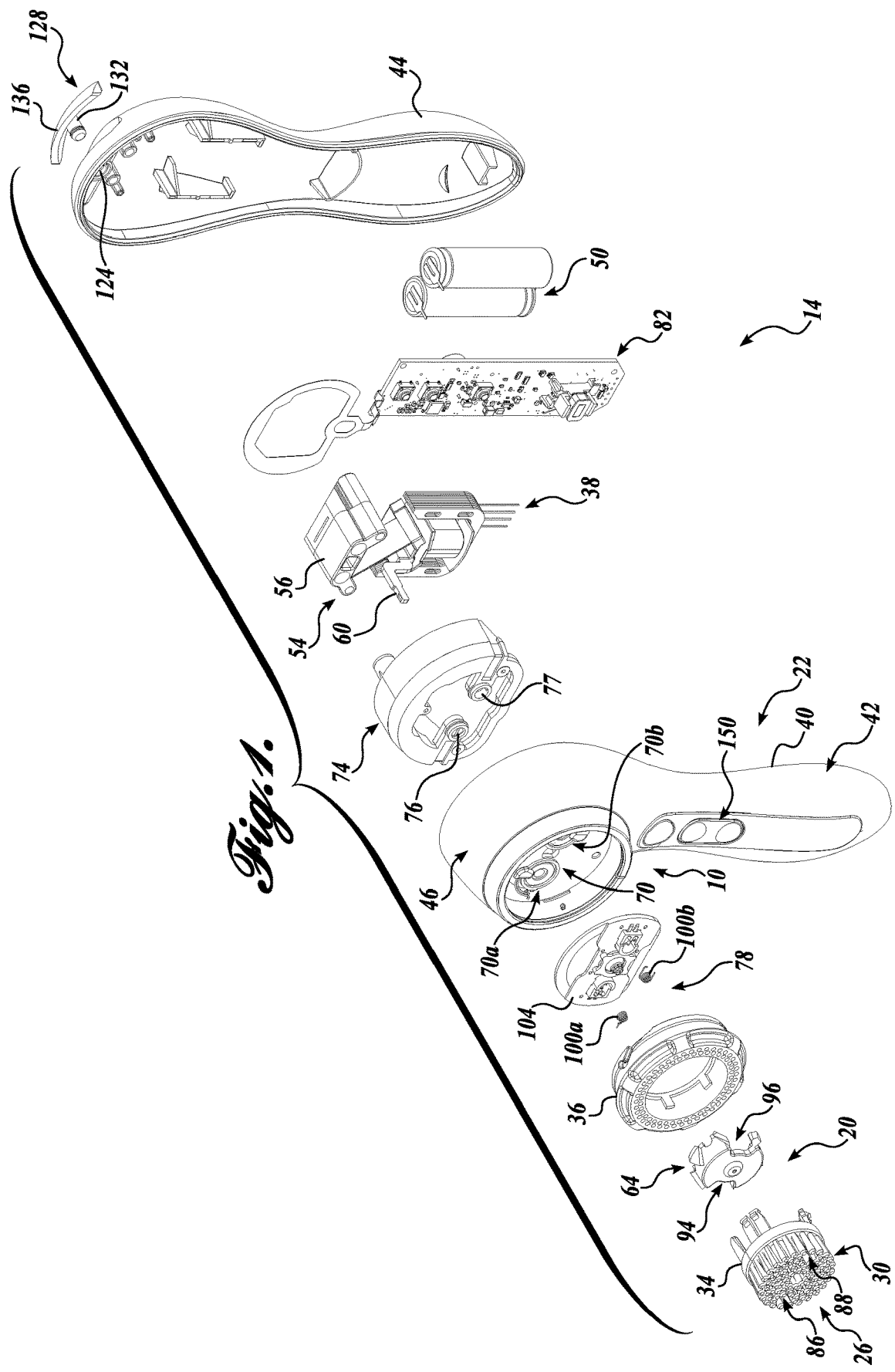
FIG. 1 is a front isometric exploded view of a personal care appliance having a vaporizing and vapor heating assembly formed in accordance with an exemplary embodiment of the present disclosure.
Figure 2:
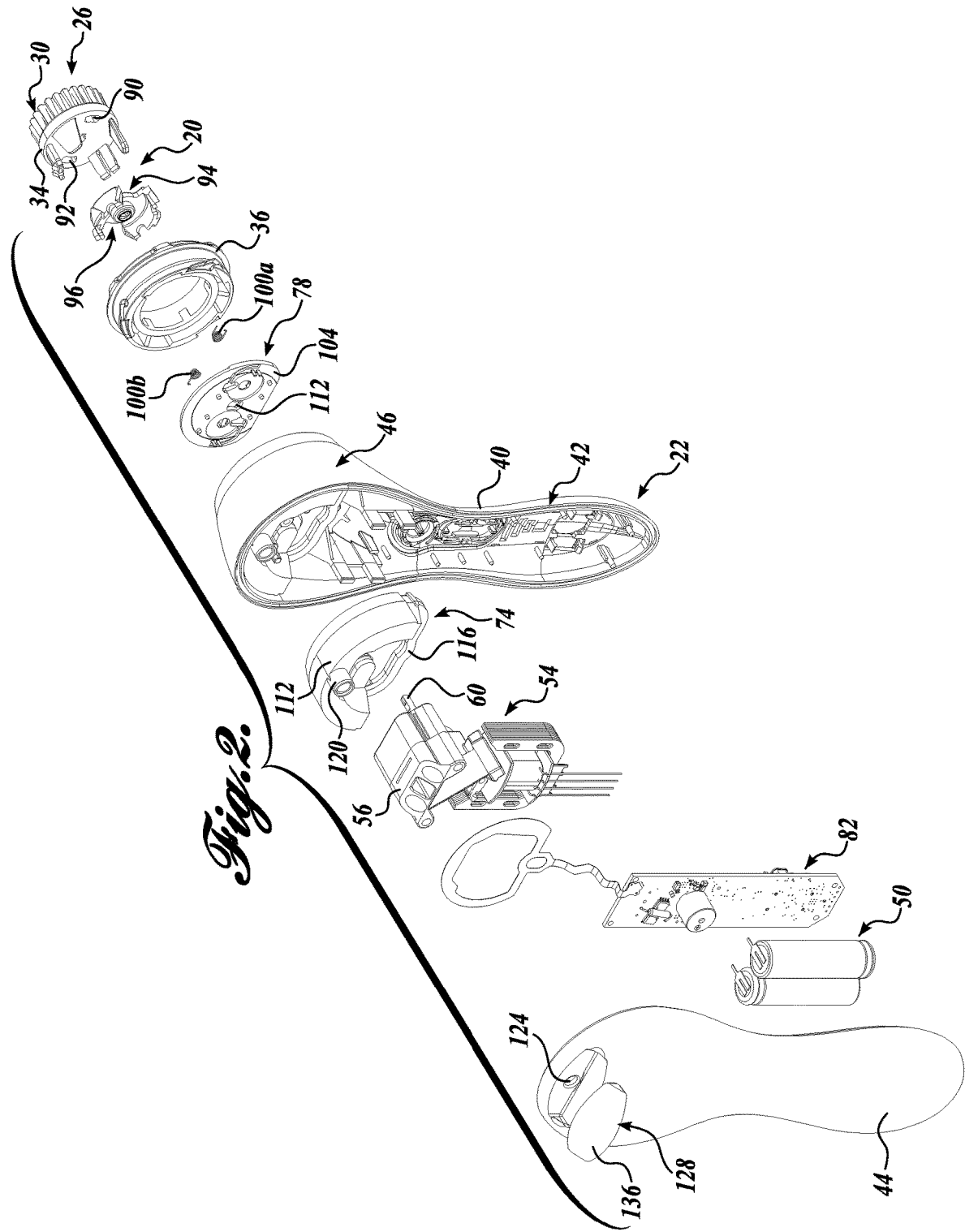
FIG. 2 is a rear isometric exploded view of the personal care appliance and vaporizing and vapor heating assembly of FIG. 1.

Heated vapor or steam machines are used for spa and at-home facial treatments to help open and unclog skin pores, remove dirt, oil and makeup, clean follicles, and provide therapeutic and detoxifying effects. Heated mist or vapor can be helpful in other applications, such as applying moist heat to an injured area of the body, heating a cosmetic formulation, medication, or other fluid before application to the body, etc.

Prior art heated vapor assemblies typically include a heating assembly that heats a reservoir of fluid, such as water, to vaporize and discharge heated fluid. However, heating some or all of the fluid in the reservoir for vaporization requires a large amount of energy. Moreover, the time required to heat the reservoir of fluid for vaporization can be unacceptable in certain applications.

FIGS. 1-4 depict an exemplary vaporizing and vapor heating assembly 10 configured to produce on-demand, heated vapor with minimal energy consumption. The vaporizing and vapor heating assembly 10 is shown embodied within an exemplary personal care appliance 14, such as a skin care appliance having a personal care head assembly 20 secured to or otherwise extending from an appliance body 22 and configured for cleansing, exfoliating, or otherwise treating a subject's skin. The personal care appliance 14, which may be employed to impart an oscillating or other driving motion to the head assembly 20, will first be described in some detail to provide context for the vaporizing and vapor heating assembly 10. However, it should be appreciated that the vaporizing and vapor heating assembly 10 may be incorporated into any suitable appliance or may instead be used independently of an appliance, and accordingly, the descriptions and illustrations provided herein should not be seen as limiting the scope of the claimed subject matter.

Referring to FIGS. 1-4, the appliance body 22 includes a front cover 40 and a rear cover 44 that, when secured together (see FIG. 4), define a handle portion 42 and a head attachment portion 46. The head attachment portion 46 is configured to selective attach a head, such as the head assembly 20, to the appliance body 22.

The exemplary head assembly 20 is removably attachable to the appliance body 22 and includes a personal care portion 26 that can be oscillated or otherwise moved over a subject's skin in order to clean, exfoliate, or otherwise treat the skin. In the depicted embodiment, the personal care portion 26 includes an inner bristle assembly 30 extending from and secured to the exterior surface of a base 34 in a manner well known in the art. The personal care portion 26 may further include an outer housing 36 that is securable to the head attachment portion 46 (through a suitable locking assembly), which may include an outer bristle assembly (not shown).

It should be appreciated that the personal care portion 26 of the head assembly 20 may instead include any other suitable structure for cleaning, exfoliating, or otherwise treating the skin or body, such as a sponge, an infusion tip, a hair brush, an exfoliating disc with one or more abrasive sections, etc. Further, the personal care portion 26 may instead be configured to treat materials other than a subject's body, such as clothing, food, etc. In addition, the head assembly 20 may instead be permanently secured to the appliance body 22.

The interior surface of the base 34, opposite the personal care portion 26, is securable on a hub 64 that is configured to interface with the drive assembly 38 disposed within the appliance body 22 for selective oscillation or otherwise driving of the head assembly 20. The drive assembly 38 in some embodiments includes an electric drive motor 54 that drives an attached head, such as head 20 assembly, via a drive shaft or armature 60. The drive assembly 38 may be configured to operate the head assembly 20 at sonic frequencies, typically in the range of 80-160 Hz, oscillating the head assembly 20 back and forth within a range or amplitude of 3-20 degrees. In some embodiments, the head assembly 20 is operated in loaded or unloaded conditions at frequencies between about 80 Hz to 120 Hz with an amplitude or range of about 3-17 degrees. In other embodiments, the head assembly 20 is operated in a loaded condition at frequencies of about 94 Hz to 106 Hz, amplitudes of about 8-12 degrees, and a duty cycle of about 38-44%.

One example of a drive assembly 38 that may be employed by the appliance 14 to oscillate the head assembly 20 is shown and described in U.S. Pat. No. 7,786,626, the disclosure of which is hereby incorporated by reference in its entirety. However, it should be understood that this is merely an example of the structure and operation of one such appliance and that the structure, operation frequency and oscillation amplitude of such an appliance could be varied, depending in part on its intended application and/or characteristics of the head, such as its inertial properties, etc. In some embodiments of the present disclosure, the frequency ranges are selected so as to drive the attached head at near resonance. Thus, selected frequency ranges are dependent, in part, on the inertial properties of the attached head. It will be appreciated that driving the attached head at near resonance provides many benefits, including the ability to drive the attached head at suitable amplitudes in loaded conditions (e.g., when contacting the skin). For a more detailed discussion on the design parameters of the appliance, please see U.S. Pat. No. 7,786,626.

The exemplary personal care appliance 14 is configured for cleansing the skin or the like. Such use typically involves the use of cleansing formulas, water, etc., applied to the head assembly 20. In that regard, in one embodiment, the personal care appliance 14 includes a "wet side" exterior of the appliance body 22, and a "dry side" interior of the appliance body 22. The head assembly 20 and certain elements of the vaporizing and vapor heating assembly 10 are therefore suitably configured to operate when wet. In that regard, suitable sealing mechanisms are used to prevent fluid leakage from the wet side to the dry side, and the components of the vaporizing and vapor heating assembly 10 are suitably secured to the front cover 40 or other areas of the appliance body 22 in a manner that prevents fluid leakage from the wet side to the dry side.

While the personal care appliance 14 is one type of appliance that can be practiced with the exemplary head assembly 20, it will be appreciated that the head assembly 20 is suitable for use with a wide range of oscillatory or vibratory motion generating devices or the like. Likewise, the personal care appliance 14 may be used with any suitable head assembly. Moreover, the vaporizing and vapor heating assembly 10 may be used with any suitable appliance with or without a head assembly.

Figure 3:
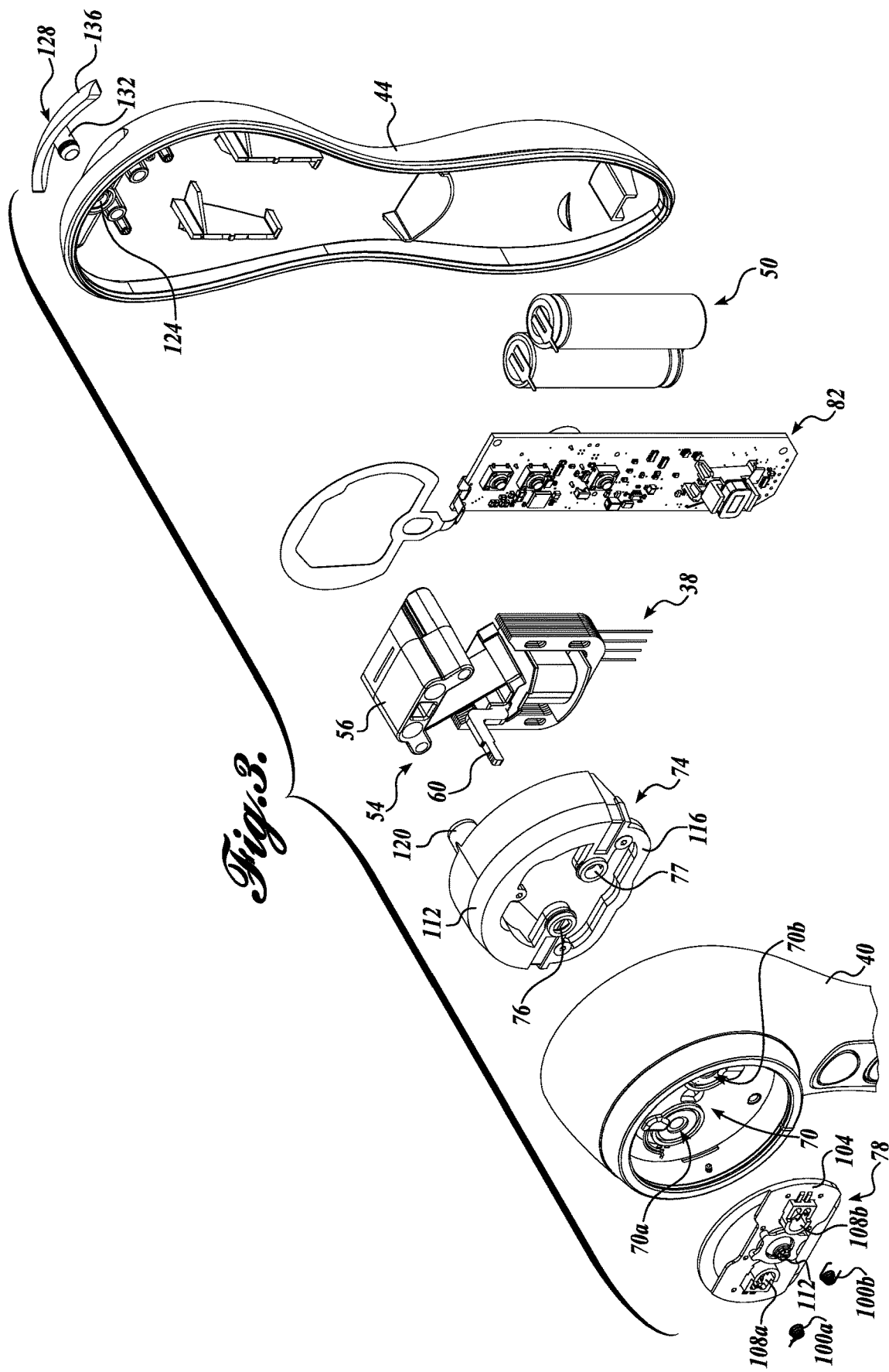
FIG. 3 is a front isometric exploded view of the vaporizing and vapor heating assembly of FIG. 1.
Figure 4:
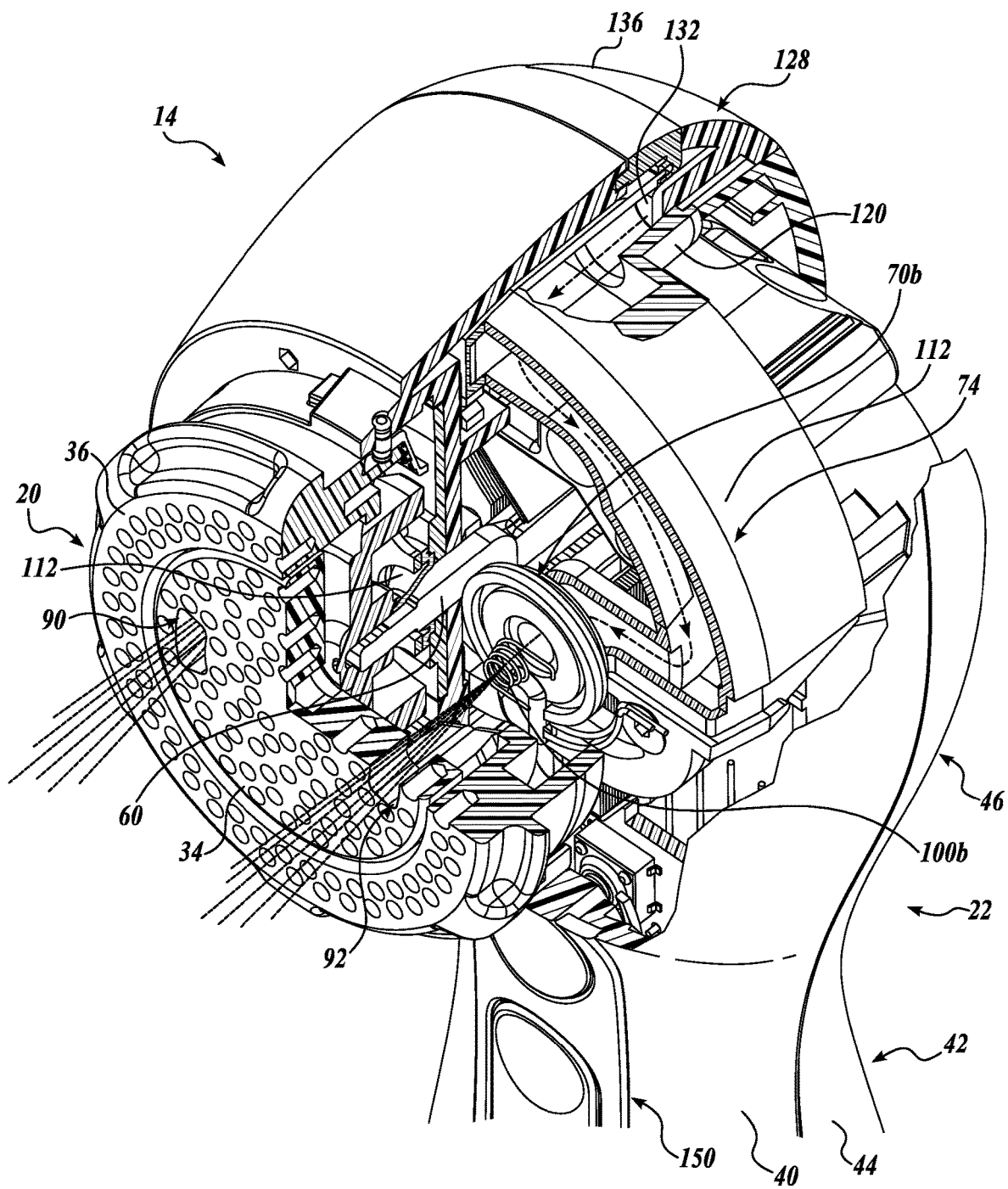
FIG. 4 is an isometric partial cross-sectional view of the personal care appliance and vaporizing and vapor heating assembly of FIG. 1, depicting an exemplary fluid flow path.

Referring to FIG. 3, a vaporizing and vapor heating assembly 10 formed in accordance with an exemplary embodiment of the present disclosure and configured for use with the personal care appliance 14 or any other suitable appliance will now be described in detail. As noted above, the vaporizing and vapor heating assembly 10 is configured to produce on-demand, heated vapor with minimal energy consumption. The terms "vapor," "vaporize," "vaporizing," etc., should be construed to include atomizing, misting, reducing to fine particles or spray, etc.

The vaporizing and vapor heating assembly 10 generally includes at least one vaporizing element 70 fluidically coupled to a reservoir assembly 72 and configured to discharge vapor, and a heater assembly 78 operably coupled to the at least one vaporizing element 70, wherein the heater assembly 78 includes at least one heating element configured to heat the discharged vapor. In the depicted embodiment, the at least one vaporizing element 70 is a piezoelectric element, specifically sometimes referred to as a piezo ultrasonic atomizer, an ultrasonic water atomizer, a piezo atomizer, a piezoelectric atomizer, etc. (hereinafter referred to as a "piezoelectric element"). However, it should be appreciated that in other applications, the at least one vaporizing element 70 may take other forms, such as a jet nebulizer, a mesh nebulizer, an ultrasonic nebulizer, or the like. In an embodiment, the vaporizing and vapor heating assembly 10 includes one or more of an actuator, a valve, a controllable aperture, an electromechanical orifice, an aperture diaphragm, an electromechanical port, an electronic oscillator for controlling a nebulizer, an ultrasonic vibrating mesh, an electromechanical spray valve, and the like.

In one embodiment, the vaporizing and vapor heating assembly 10 includes first and second vaporizing elements 70a and 70b fluidically coupled to first and second outlet openings 76 and 78 in at least one reservoir 74 of the reservoir assembly 72. However, in other embodiments, only one vaporizing element is used, and yet in other embodiments, three or more vaporizing elements are used. The first and second vaporizing elements 70a and 70b are secured to the wet side of the appliance body 22 within an exterior recessed area of the head portion 46 of the front cover 40 in a suitable manner to prevent any fluid leakage from the wet side of the appliance 14 to the dry side. For instance, the first and second vaporizing elements 70a and 70b may be secured within the exterior recessed area of the head portion 46 by ultrasonic welding, insert molding, or the like. Furthermore, the first and second vaporizing elements 70a and 70b are electrically connected to operating structure of the personal care appliance 14, such as a printed circuit board (PCB) 82 and/or other suitable circuitry, in a manner well known in the art.

In one embodiment, the first and second vaporizing elements 70a and 70b are positioned within the head portion 46 of the appliance body 22 to discharge vapor through the head assembly 20. In that regard, the head assembly 20 includes suitable discharge vapor openings for allowing the discharged vapor to pass through the head assembly 20. The depicted head assembly 20 includes first and second open bristle areas 86 and 88 in the inner bristle assembly 30 (see FIG. 1), which are aligned with first and second base openings 90 and 92 in the base 34 (see FIG. 4, where the inner bristle assembly 30 is not shown for clarity), which are aligned with first and second hub openings or cutouts 94 and 96 in the hub 64 when the personal care portion 26 is secured on the hub 64. As such, the discharged vapor from the first and second vaporizing elements 70a and 70b may pass through the hub 64 and the personal care portion 26. The first and second open bristle areas 86 and 88, first and second base openings 90 and 92, first and second hub cutouts 94 and 96 may be sufficiently large such that the vapor may be discharged through the head assembly 20 both when the head assembly 20 is still (i.e., not turned on) and when the head assembly 20 is oscillating.

In the depicted embodiment, the first and second open bristle areas 86 and 88, first and second base openings 90 and 92, and first and second hub cutouts 94 and 96 are at substantially 9 o'clock and 3 o'clock positions of the head assembly 20. In that regard, the head assembly 20 may include keyed structure to ensure that the personal care portion 26 is appropriately mounted to the hub 64 such that the first and second open bristle areas 86 and 88 and the first and second base openings 90 and 92 are aligned. Similarly, the outer housing 36 and/or head assembly 20 may include keyed structure to ensure that the head assembly 20 is appropriately mounted to the outer housing 36 such that the first and second open bristle areas 86 and 88, the first and second base openings 90 and 92, and the first and second hub cutouts 94 and 96 are aligned.

In another embodiment, the first and second vaporizing elements 70a and 70b may be positioned within the head portion 46 to discharge vapor through another portion of the head assembly 20 (such as through a central opening, through three openings at 4, 8, and 12 o'clock positions, through four openings at 3, 6, 9, and 12 o'clock positions, etc.), through a portion of the outer housing 36, or instead through a portion of the appliance body 22. If positioned to discharge vapor through the outer housing 36, it should be appreciated that suitable opening(s) may be formed in the outer housing 36 and/or the outer bristle assembly (not shown) extending from the outer housing 36. Likewise, if positioned to discharge vapor through the appliance body 22, suitable opening(s) may be formed in the appliance body 22. It should be appreciated that the vapor may be discharged through any suitable portion of the personal care appliance 14. Such alternative configurations may simplify or negate any keying structure needed between the personal care portion 26, the hub 64, and/or the outer housing 36 for aligning the discharge vapor openings.

The vapor discharged from the at least one vaporizing element 70 is heated with the heater assembly 78. In that regard, an exemplary embodiment of the heater assembly 78, which is operably coupled to the at least one vaporizing element 70, and which includes at least one heating element 100 configured to heat the discharged vapor, will now be described. The heater assembly 78 is positioned relative to the at least one vaporizing element 70 such that it heats the vapor as it is discharged from the at least one vaporizing element 70. In this manner, only the discharged vapor is heated, rather than pre-heating an entire reservoir of fluid contained in a reservoir.

In that regard, the heater assembly 78 includes at least one heating element, and in the depicted embodiment, first and second heating elements 100a and 100b secured to the wet side of the appliance body 22 and positioned relative to the first and second vaporizing elements 70a and 70b to heat the vapor discharged therefrom. The first and second heating elements 100a and 100b may be positioned relative to the first and second vaporizing elements 70a and 70b in any suitable manner. For instance, in the depicted embodiment, the first and second heating elements 100a and 100b are secured on a first side of a heating assembly base 104 that overlies the first and second vaporizing elements 70a and 70b. In that regard, the heating assembly base 104 has a shape that substantially corresponds to the shape of the exterior recessed area of the head portion 46 of the front cover 40. Moreover, the heating assembly base 104 may include suitable vaporizing element cavities (not labeled) defined within a second side (opposite the heating elements 100a and 100b) that receive/mate with the first and second vaporizing elements 70a and 70b to help ensure proper alignment during assembly and use. The heating assembly base 104 is secured within the exterior recessed area of the head portion 46 in any suitable manner. It should be appreciated that the first and second heating elements 100a and 100b may be positioned relative to the first and second vaporizing elements 70a and 70b in any other manner. Moreover, if more or less than two vaporizing elements are used, a corresponding number of heating element(s) could be positioned relative to the vaporizing element(s) or another suitable number of heating element(s) may be used.

The first and second heating elements 100a and 100b are secured to the heating assembly base 104 in any suitable manner. For instance, the first and second heating elements 100a and 100b may be press-fit, insert molded, welded, or otherwise secured within first and second heating element housings 108a and 108b defined on the first side of the heating assembly base 104. The first and second heating element housings 108a and 108b may be configured to both secure the first and second heating elements 100a and 100b to the heating assembly base 104 as well as electrically connect the first and second heating elements 100a and 100b to the PCB 82 or other operating structure or circuitry of the appliance 14. The heating assembly base 104 also includes a suitable sealed opening 112 for receiving the drive shaft 60 of the drive assembly 38. However, it should be appreciated that a sealed opening may instead be defined in the front cover 40 or another portion of the appliance 14.

Any suitable heating element 100 may be used to heat the vapor as it is discharged from the at least one vaporizing element 70. In the depicted exemplary embodiment, the first and second heating elements 100a and 100b are tapered coils that generate heat when supplied with power. In that regard, the first and second heating elements 100a and 100b are electrically connected to operating structure of the personal care appliance 14, such as the PCB 82, in a manner well known in the art. The heating assembly 78 may be supplied with temperature sensors to detect and output the temperature of the heating elements 100a and 100b for controlling the vaporizing and vapor heating assembly 10.

In one embodiment, the tapered coils are positioned relative to the first and second vaporizing elements 70a and 70b such that the discharged vapor passes substantially through the middle opening of the corresponding tapered coil. In that regard, the vapor leaving the vaporizing element transforms from a mist to a heated stream of vapor as it exits the appliance 14. Heating the discharged vapor causes thermal expansion of the vapor, thereby increasing the velocity of the discharged vapor. In effect, the discharged, heated vapor can be more forcefully discharged from the appliance 14 than would otherwise occur with standard misting assemblies that pre-heat the fluid before vaporization. Additional nozzles or nozzle assemblies (not shown) may be used to help increase the velocity of the heated discharged vapor. For instance, an atomizing nozzle, a shaped nozzle, a venturi-style nozzle or the like may be secured over each tapered coil to increase the velocity of the heated discharged vapor as it leaves the tapered coil.

As noted above, in one embodiment, the first and second vaporizing elements 70a and 70b of the vaporizing and vapor heating assembly 10 are fluidically coupled to first and second outlet openings 76 and 77 in the reservoir 74 of the reservoir assembly 72. The reservoir assembly 72 may include a single reservoir 74 having first and second outlet openings 76 and 78, as in the depicted embodiment, or the reservoir assembly 72 may instead include multiple reservoirs each having one or more openings for connection to one or more vaporizing elements. In an embodiment with multiple reservoirs, a first reservoir could be configured to contain a first type of fluid and a second reservoir could be configured to contain a second type of fluid. The fluids could chemically react when vaporized and heated to cause a desired effect on the face or other treatment area. The fluids themselves may release energy when combined (i.e., an exothermic reaction), which may further enhance the warming sensation felt by a user when using the heated vaporizing assembly 10.

The first and second outlet openings 76 and 77 in the reservoir 74 are sealingly and fluidically coupled to the first and second vaporizing elements 70a and 70b in any suitable manner. For instance, the reservoir 74 may be ultrasonically welded to the wet (interior) side of the front cover 40 to place the first and second outlet openings 76 and 77 of the reservoir 74 in fluid communication with the first and second vaporizing elements 70a and 70b. Suitable sealing elements or the like may be disposed therebetween.

The reservoir 74, which may be shaped to conform to the body 22, may also be shaped to ensure that the fluid can flow out of both outlet openings 76 and 78 when oriented for use (such as in a substantially upright or vertical orientation depicted in the FIGURES). In that regard, the reservoir 74 includes a substantially C-shaped first main portion 112 for holding the majority of fluid within the reservoir 74, and a substantially C-shaped second connecting portion 116 extending between opposite curved ends of the main portion 112, wherein the combined substantially circular reservoir shape allows the drive shaft 60 to pass therethrough. The first and second outlet openings 76 and 78 are located generally between the intersection of the main portion 112 and the connecting portion 116 and are positioned to be placed into fluid communication with the first and second vaporizing elements 70a and 70b. The connecting portion 116 essentially acts as pipe for fluid to flow between the first and second ends of the main portion 112. In that manner, fluid will flow toward the first and second outlet openings 76 and 78 when the personal care appliance 14 is moved from any orientation (such as horizontal) into the substantially upright, vertical orientation for use.

It should be appreciated that the reservoir 74 may instead be any other shape and configuration configured to fit within the personal care appliance 14 or another suitable appliance. Moreover, if more than one reservoir were used, each reservoir may have a simpler shape with an opening at the bottom of the reservoir for ensuring that fluid can flow out of the opening when oriented for use. Accordingly, the descriptions and illustrations provided herein should not be seen as limiting.

The reservoir 74 further includes a reservoir inlet opening 120 defined at an upper end of the main portion 112 and configured for fluidic communication with a body inlet opening 124 defined in an upper end of the rear cover 44. When the body 22 of the personal care appliance 14 is assembled, the reservoir inlet opening 120 sealingly mates with the body inlet opening 124 in a suitable manner. The reservoir 74 may be filled through the body inlet opening 124 as well as emptied, for instance, by inverting the body 22 such that fluid may flow out of the opening 124.

A fill cap 128 is configured to selectively plug or otherwise close off the body inlet opening 124 in a suitable manner. For instance, the fill cap 128 may include a plug portion 132 extending from a handle portion 136, where the plug portion 132 is configured to be sealingly received within the body inlet opening 124. The handle portion 136 may be any suitable shape such that it is graspable by a user, and may nest within a recessed portion or cavity (not labeled) defined in the exterior of the rear cover 44 when closing off the body inlet opening 124.

The body inlet opening 124 may also be configured to be placed into fluidic communication with one or more external reservoirs or cartridges (with each cartridge containing one or more internal reservoirs) or conduits connecting to reservoir/cartridge(s) to provide supplemental "tank(s)" of fluid and/or to allow unique, pre-packaged reservoir/cartridge(s) of fluid to be used with the heated vaporizing assembly 10. In that regard, the body 22 may include two or more openings configured to be placed into fluidic communication with two or more reservoir/cartridge(s). In an embodiment where two or more internal reservoirs are used, each internal reservoir may be placed into fluidic communication with one or more unique, pre-packaged external reservoir/cartridges of fluid, wherein heated application of the fluids optionally results an exothermic and/or another chemical reaction. In that regard, the body openings may include nozzle portions suitable for mating with only a certain type of reservoir/cartridge(s), or other structure may be used to ensure the appropriate reservoir/cartridge(s) is mated with the corresponding opening and that no fluid from a first reservoir/cartridge enters the opening for another reservoir/cartridge (such as by using a dividing structure between the body openings or the like). In addition, the reservoir assembly 72 may include suitable circuitry for identifying each reservoir/cartridge placed into communication with a body inlet opening and suitable circuitry for sending at least one output signal indicative of the identified reservoir/cartridge(s) for controlling and/or activating the drive assembly 38 and/or the vaporizing and vapor heating assembly 10.

Figure 5:
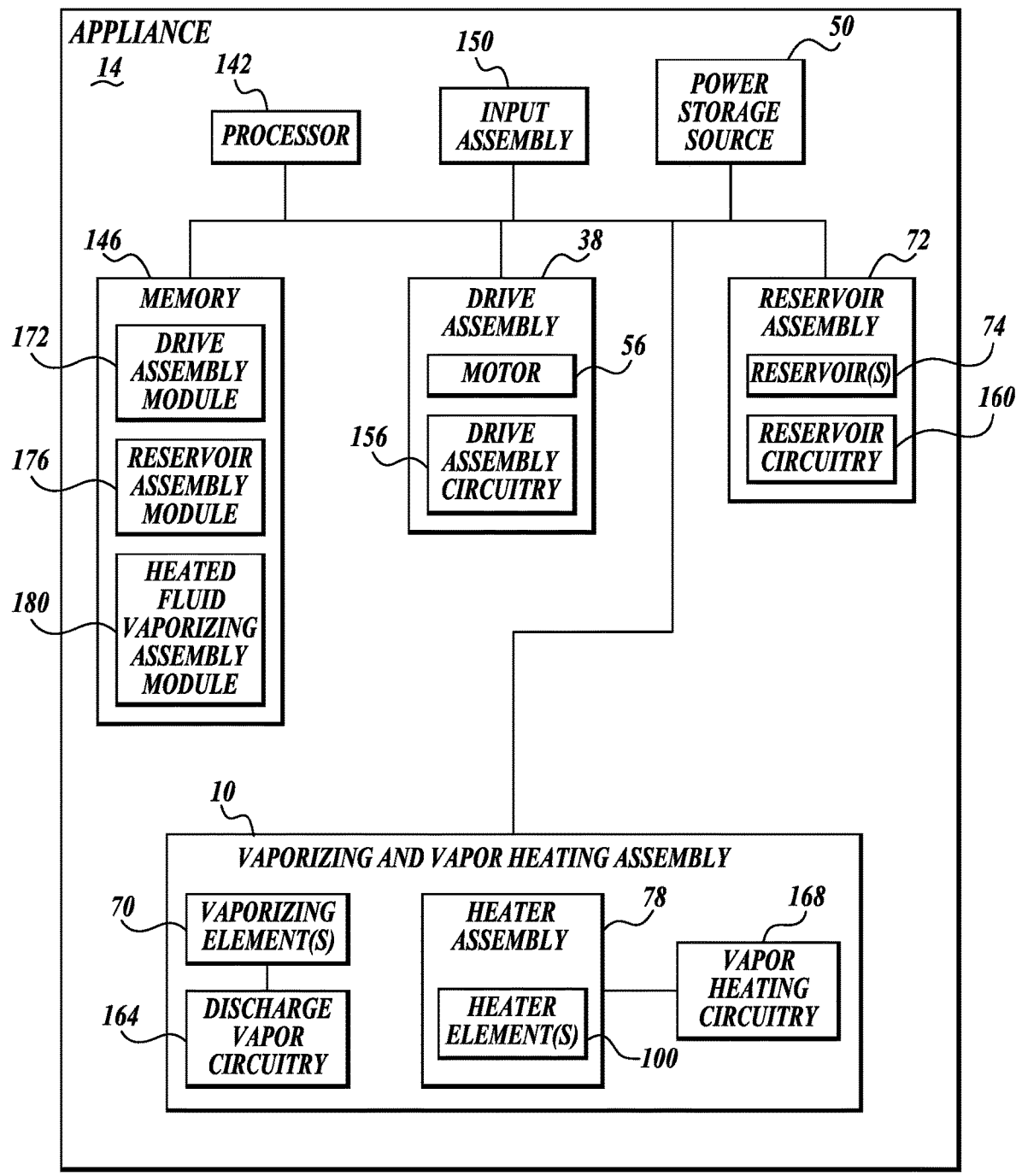
FIG. 5 is a block diagrammatic depiction of an exemplary internal operating structure of the personal care appliance and vaporizing and vapor heating assembly of FIG. 1.

In that regard, the internal operating structure of the personal care appliance 14 and its associated internal assemblies is shown in block diagrammatic form in FIG. 5. An exemplary operating structure of the appliance 14 includes a programmed microcontroller or processor 142 configured to control the delivery of power to the drive assembly 38, the vaporizing and vapor heating assembly 10, and/or the reservoir assembly 72 from the power storage source 50. Further, the processor 142 is configured to operate in accordance with program instructions stored in a memory 146 or otherwise stored in hardware format for controlling aspects of the drive assembly 38, the vaporizing and vapor heating assembly 10, and/or the reservoir assembly 72.

As illustrated in FIG. 5, in one embodiment the memory 146 stores a drive assembly module 172, a reservoir assembly module 176, and a heated fluid vaporizing module 180, wherein each module stores programs, files, etc., for activating and/or controlling at least one of the drive assembly 38, the vaporizing and vapor heating assembly 10, and/or the reservoir assembly 72. It should be appreciated that the drive assembly module 172, the reservoir assembly module 176, and the vaporizing and vapor heating assembly module 180 may be instead be defined by a single module or more than three modules. Accordingly, any suitable programs and instructions for activating and/or controlling at least one of the drive assembly 38, the vaporizing and vapor heating assembly 10, and/or the reservoir assembly 72 may be used.

The drive assembly 38 includes drive assembly circuitry 156 operably coupled to the motor 56 and configured for actuating and controlling the motor 56 to oscillate the head assembly 20 in the manner described above or in any other suitable manner. For instance, the drive assembly circuitry 156 can be configured to receive input from an input assembly 150 (which may include an on/off button, a power adjust button, a mode control button, a vaporizing button, a temperature control button, etc., as shown in FIG. 1). The input assembly 150 may be configured and arranged to selectively deliver power from the power storage source 50 to the drive assembly 38. The drive assembly module 172 may include any suitable programs, files, or instructions for activating and controlling the drive assembly 38.

The vaporizing and vapor heating assembly 10 includes discharge vapor circuitry 164 operably coupled to the vaporizing element(s) 70 and configured to activate the vaporizing element(s) 70 to generate a discharge vapor. In one embodiment, the vaporizing element(s) 70 is a piezoelectric element(s) that defines part of the discharge vapor circuitry 164. The discharge vapor circuitry 164 is configured to activate the vaporizing element(s) 70 in response to inputs received from the processor 142, inputs received from one or more modules stored in the memory 146, and/or inputs received from other assemblies (such as the input assembly 150, the drive assembly 38, the reservoir assembly 72, and/or the heater assembly 78). The vaporizing and vapor heating assembly module 180 may include any suitable programs, files, or instructions for activating and controlling the vaporizing and vapor heating assembly 10.

In one embodiment, the discharge vapor circuitry 164 may receive an input to activate the vaporizing element(s) 70 when vapor heating circuitry 168 of the heater assembly 78 outputs a signal indicating that the heating element 100 of the heater assembly 78 has reached a first predetermined temperature (such as a low threshold temperature). In such an embodiment, the vaporizing element(s) 70 will not discharge vapor until the heating element 100 has essentially pre-heated and is ready to heat the vapor when discharged.

In one embodiment, the discharge vapor circuitry 164 may further receive an input to activate the vaporizing element(s) 70 in response to at least one input indicative of a vapor discharge rate. For instance, the input assembly 150 may be used to select a vapor discharge mode, velocity, etc., and instructions may be sent to the discharge vapor circuitry 164 to discharge vapor in a selectively controlled manner based on input(s) selected through the input assembly 150. In some embodiments, instructions may be sent from the reservoir assembly module 176 to the discharge vapor circuitry 164 to discharge vapor in a selectively controlled manner based on an identified reservoir/cartridge connected to the appliance 14 or otherwise fluidically connected to the reservoir(s) 74 or the vaporizing element(s) 70.

The discharge vapor circuitry 164 may further be configured to generate an output signal indicative of the activation of the vaporizing element(s) 70. For instance, the discharge vapor circuitry 164 may output a signal indicating that the vaporizing element(s) 70 have been activated such that the heater assembly 78 may activate the heating element(s) 100 in response to such signal (or processed signal). In some embodiments, the discharge vapor circuitry 164 may include a timer and may output a signal indicating when the vaporizing element(s) 70 has been activated for a predetermined amount of time.

It should be appreciated that the discharge vapor circuitry 164 may be configured to receive any suitable input signals for controlling aspects of the vaporizing element(s) 70. In that regard, the discharge vapor circuitry 164 may also be configured to output any signals in response to activation of the vaporizing element(s) 70 for activating or controlling other assemblies, such the drive assembly 38, the reservoir assembly 72, or the heater assembly 78.

The vaporizing and vapor heating assembly 10 further includes vapor heating circuitry 168 operably coupled to the heating element(s) 100 and configured to activate the heating element(s) 100 to heat the discharged vapor. In one embodiment, the heating element(s) 100 define part of the vapor heating circuitry 168.

The vapor heating circuitry 168 is configured to activate the heating element(s) 100 in response to inputs received from the processor 142, inputs received from one or more modules stored in the memory 146, inputs received from other circuitry, such as the discharge vapor circuitry 164, and/or inputs received from other assemblies (such as the input assembly 150, the drive assembly 38, and/or the reservoir assembly 72). For instance, the vapor heating circuitry 168 may receive an input to activate the heating element(s) 100 upon activation of the vaporizing element(s) 70. In that manner, the heating element(s) 100 will not overheat since heat exchange will occur between the heating element(s) 100 and the discharged vapor.

In one embodiment, the vapor heating circuitry 168 may further receive an input to activate the heating element(s) 100 in response to at least one input indicative of a selected heat level. For instance, the input assembly 150 may be used to select a heat mode (e.g., low, medium, high), and instructions may be sent to the vapor heating circuitry 168 to activate the heating element(s) 100 in a selectively controlled manner. In some embodiments, instructions may be sent from the reservoir assembly module 176 to the vapor heating circuitry 168 to heat the discharged vapor in a selectively controlled manner based on an identified reservoir/cartridge connected to the appliance 14 or otherwise fluidically connected to the reservoir(s) 74.

The vapor heating circuitry 168 may further include circuitry configured to deactivate the heater element(s) 100 when it reaches a second predetermined temperature (such as a high threshold temperature). In that regard, the vapor heating circuitry 168 may include one or more temperature sensors configured to output the temperature of the heater element(s) 100. The vapor heating circuitry 168 may further be configured to generate an output signal indicative of the activation of the heater element(s) 100 and/or the temperature of the heater element(s) 100. For instance, the vapor heating circuitry 168 may output a signal indicating that the heating element(s) 100 have been activated (or reached a predetermined temperature) such that the discharge vapor circuitry 164 may activate the vaporizing element(s) 70 in response to such signal (or processed signal). In some embodiments, the vapor heating circuitry 168 may include a timer that outputs a signal indicating when the heating element(s) 100 has been activated for a predetermined amount of time and circuitry for inactivating the heating element(s) 100 upon receipt of such signal.

It should be appreciated that the vapor heating circuitry 168 may be configured to receive any suitable input signals for controlling aspects of the heating element(s) 100. In that regard, the vapor heating circuitry 168 may also be configured to output signals in response to activation of the heating element(s) 100 for activating or controlling other assemblies, such the drive assembly 38, the reservoir assembly 72, and/or the discharge vapor circuitry 164.

The reservoir assembly 72 may include reservoir circuitry 160 operably coupled to the reservoir(s) 74 and/or configured to be operably coupled to external reservoir/cartridge(s) for identifying each reservoir/cartridge placed into communication with a body inlet opening. In that regard, the reservoir circuitry 160 may output signals indicative of an identified reservoir/cartridge(s) for activating or controlling the drive assembly 38 and/or the vaporizing and vapor heating assembly 10. For instance, the reservoir circuitry 160 may output a signal(s) indicating that first and second cartridges have been identified (e.g., placed into communication with a body inlet opening of the appliance 14). The output signals may be processed by the processor 142, and in response, the processor 142 may output one or more signals to the drive assembly 38 or the vaporizing and vapor heating assembly 10. As a specific example, if the fluids contained in the identified cartridges will chemically react upon mixing or are otherwise heat activated, one or more input signals may be sent to the vaporizing and vapor heating assembly 10 for controlling the vapor discharge rate and/or the heat output of the heating element(s) 100, and/or one or more input signals may be sent to the drive assembly 38 to control the frequency of the oscillating head 20. In that regard, the output of the reservoir circuitry 160 may be used to help ensure that the vaporizing and vapor heating assembly 10 and/or the drive assembly 38 are safely and appropriately used with the fluids contained in the identified reservoir/cartridge(s).

The detailed description set forth above in connection with the appended drawings is intended as a description of exemplary embodiments of the vaporizing and vapor heating assembly 10 and a personal care appliance 14 having a vaporizing and vapor heating assembly 10, and are not intended to represent the only embodiments. The representative embodiments described in this disclosure are provided merely as an example or illustration and are not intended to be exhaustive or to limit the claimed subject matter to the precise forms disclosed.

In the foregoing description, numerous specific details are set forth in order to provide a thorough understanding of the exemplary embodiments of the present disclosure. It will be apparent to one skilled in the art, however, that the exemplary embodiments of the present disclosure may be practiced without some or all of the specific details. In some instances, well-known process steps or features have not been described in detail in order not to unnecessarily obscure various aspects of the present disclosure. Further, it will be appreciated that the exemplary embodiments of the present disclosure may employ any combination of features described herein.

The present disclosure may also include references to directions, such as "forward," "rearward," "front," "back," "upward," "downward," "lateral," "medial," "in," "out," "extended," "advanced," "retracted," "vertical," "horizontal," "proximal," "distal," "central," etc. These references, and other similar references in the present disclosure, are only to assist in helping describe and understand the particular embodiment and are not intended to limit the present disclosure to these directions or locations.

The present disclosure may also reference quantities and numbers. Unless specifically stated, such quantities and numbers are not to be considered restrictive, but exemplary of the possible quantities or numbers associated with the present disclosure. Also in this regard, the present disclosure may use the term "plurality" to reference a quantity or number. In this regard, the term "plurality" is meant to be any number that is more than one, for example, two, three, four, five, etc. In an embodiment, "about," "approximately," etc., means plus or minus 5% of the stated value.

Thus, while illustrative embodiments have been illustrated and described, it will be appreciated that various changes can be made therein without departing from the spirit and scope of the invention.

The embodiments of the invention in which an exclusive property or privilege is claimed are defined as follows:

1. A vaporizing and vapor heating assembly, comprising:
at least one reservoir includes a first portion and a second portion that together form a substantially ring-shaped chamber having a front side, a back side, and an opening within a center of the ring-shaped chamber, wherein the opening extends from the front side to the back side of the ring-shaped chamber, and a radially inward leading passage extends from the ring-shaped chamber toward the center, wherein the first portion holds more volume than the second portion, and wherein a drive assembly is connected to a head assembly through the opening in the ring-shape chamber:
at least one vaporizing element, configured to discharge a vapor, is fluidically coupled to the radially inward leading passage, wherein the at least one vaporizing element is positioned toward the center of the ring-shaped chamber; and
a heater assembly configured to heat the discharged vapor, the heater assembly including at least one tapered coil positioned in front of the at least one vaporizing element such that the discharged vapor passes through the at least one tapered heating element in a direction from a first opening in the tapered coil to a second smaller opening in the tapered coil; and
a controller configured to supply heated vapor on-demand by contacting the vapor on the tapered coil.

2. The assembly of claim 1, wherein the at least one vaporizing element is a piezoelectric element.

3. The assembly of claim 2, wherein the piezoelectric element is in fluid communication with the at least one reservoir containing a fluid.

4. The assembly of claim 1, further comprising a replaceable cartridge including one or more cartridge reservoirs fluidically coupled to the at least one vaporizing element.

5. The assembly of claim 4, further comprising a discharge vapor circuitry operably coupled to the at least one vaporizing element and configured to generate a discharge vapor responsive to one or more inputs indicative of a cartridge identification.

6. The assembly of claim 1, further comprising:
a discharge vapor circuitry operably coupled to the at least one vaporizing element and configured to generate a discharge vapor; and
a vapor heating circuitry operably coupled to the heater assembly and configured to heat the discharged vapor.

7. The assembly of claim 6, wherein the discharge vapor circuitry comprises one or more piezo ultrasonic atomizers configured to discharge vapor from the at least one reservoir responsive to at least one input indicative of a discharge rate.

8. The assembly of claim 6, wherein the vapor heating circuitry activates the heater assembly responsive to at least one input indicative of activation of the at least one vaporizing element.

9. The assembly of claim 6, wherein the vapor heating circuitry includes at least one heating element configured to be heated between at least first and second temperatures.

10. The assembly of claim 9, wherein the discharge vapor circuitry is configured to activate the at least one vaporizing element when the at least one heating element reaches the first temperature.

11. The assembly of claim 9, wherein the discharge vapor circuitry is configured to deactivate the heater assembly when the at least one heating element reaches the second temperature.

12. A personal care appliance, comprising:
an appliance body having a personal care portion and a circuitry configured to impart a driving motion to the personal care portion;
at least one reservoir includes a first portion and a second portion that together form a substantially ring-shaped chamber having a front side, a back side, and an opening within a center of the ring-shaped chamber, wherein the opening extends from the front side to the back side of the ring-shaped chamber, and a radially inward leading passage extends from the ring-shaped chamber toward the center, wherein the first portion holds more volume than the second portion, and wherein a drive assembly is connected to a head assembly through the opening in the ring-shape chamber;
at least one vaporizing element, configured to discharge a vapor, is fluidically coupled to the radially inward leading passage, wherein the at least one vaporizing element is positioned toward the center of the ring-shaped chamber; and
a heater assembly configured to heat the discharged vapor, the heater assembly including at least one tapered heating element electrically connected to the circuitry of the personal care appliance and positioned in front of the at least one vaporizing element such that the vapor passes through the at least one tapered heating element when discharged; and
a controller configured to supply heated vapor on-demand by contacting the vapor on the heating element.

13. The appliance of claim 12, further comprising:
a circuitry configured to exchange an encrypted and anonymized personal care appliance information with a remote network.

14. The appliance of claim 12, further comprising:
a circuitry configured to detect a client device associated with the personal care appliance and to exchange an encrypted and anonymized information with the client device.

15. The appliance of claim 12, further comprising:
a circuitry configured to detect a client device associated with the personal care appliance and to exchange vaporizing element control information with the client device.

16. The appliance of claim 12, wherein the at least one heating element is a tapered coil positioned in front of the at least one vaporizing element such that the vapor passes through the tapered coil when discharged in a direction from a first opening in the tapered coil to a second smaller opening in the tapered coil.

17. The appliance of claim 12, further comprising a replaceable cartridge including one or more cartridge reservoirs fluidically coupled to the at least one vaporizing element.

18. The appliance of claim 17, further comprising a discharge vapor circuitry operably coupled to the at least one vaporizing element and configured to generate a discharge vapor responsive to one or more inputs indicative of a cartridge identification.

19. The appliance of claim 12, wherein the ring-shaped chamber includes a first substantially C-shaped main portion and a second substantially C-shaped connecting portion extending between opposite curved ends of the first substantially C-shaped main portion, wherein the second substantially C-shaped portion allows fluid to flow between the first and second ends of the main portion, wherein at least one outlet opening for fluidically connecting to the at least one vaporizing element is defined between the intersection of the first substantially C-shaped main portion and the second substantially C-shaped connecting portion.

* * * * *